(12) United States Patent
Nirchio

(10) Patent No.: US 6,344,460 B1
(45) Date of Patent: Feb. 5, 2002

(54) PROPYNYL URACILS

(75) Inventor: Peter C. Nirchio, Lebanon, NJ (US)

(73) Assignee: Lonza Inc., Fair Lawn, NJ (US)

( * ) Notice: Subject to any disclaimer, the term of this patent is extended or adjusted under 35 U.S.C. 154(b) by 0 days.

(21) Appl. No.: 09/524,412

(22) Filed: Mar. 13, 2000

(51) Int. Cl.$^7$ .................. C07D 239/54; C07D 239/545; C07D 239/553; A61K 31/513
(52) U.S. Cl. ................. 514/274; 544/309; 544/310; 544/311; 544/312; 544/313; 544/314
(58) Field of Search ............................ 544/309, 310, 544/311, 312, 313, 314; 514/274

(56) References Cited

U.S. PATENT DOCUMENTS

| | | | |
|---|---|---|---|
| 3,235,363 A | 2/1966 | Luckenbaugh et al. | 71/2.5 |
| 3,330,640 A | 7/1967 | Luckenbaugh et al. | 71/92 |
| 5,116,404 A | 5/1992 | Ishii et al. | 71/92 |
| 5,127,935 A | 7/1992 | Satow et al. | 71/92 |
| 5,354,730 A | 10/1994 | Enomoto et al. | 504/243 |
| 5,356,863 A | 10/1994 | Satow et al. | 504/243 |
| 5,645,985 A | 7/1997 | Froehler et al. | 435/6 |
| 5,767,264 A | 6/1998 | Ötvös et al. | 536/245 |

FOREIGN PATENT DOCUMENTS

| | | |
|---|---|---|
| CH | 482402 A | 12/1969 |
| EP | 05 39114 A2 | 4/1993 |
| EP | 05 39114 A3 | 4/1993 |
| EP | 438209 | 9/1994 |

OTHER PUBLICATIONS

Hisa, et al., Nucleosides & Nucleotides, 15(1–3), 85–96 (1996).
Lazrek, et al., Nucleosides & Nucleotides, 17(9–11), 1851–1856 (1998).
Krivonogov, V. P. et al., Zh. Prikl. Khim., 70(2):315–320 (1997).
Kundu, Nitya G. et al., J. Pharm. Sci., 71(8):935–8 (1982).

Primary Examiner—John M. Ford
(74) Attorney, Agent, or Firm—Darby & Darby

(57) ABSTRACT

The present invention provides compounds comprising propynyl uracils having the formula

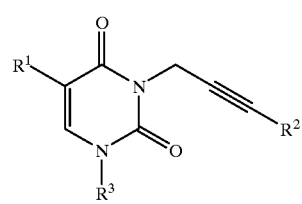

I wherein $R^1$ is hydrogen, chlorine, bromine, iodine, fluorine, —CN, substituted or unsubstituted linear or branched $C_1$–$C_4$ alkyl, —$NO_2$, methoxy, ethoxy, n-propoxy, or iso-propoxy; $R^2$ is iodine or bromine; and $R^3$ is propynyl, 3-iodopropynyl, 3-bromopropynyl, substituted or unsubstituted 2-furanyl, substituted or unsubstituted 3-furanyl, substituted or unsubstituted 2-pyrrolidinyl, substituted or unsubstituted 3-pyrrolidinyl, D-ribose, or deoxyribose. Another embodiment of the invention encompasses propynyl uracils having the formula

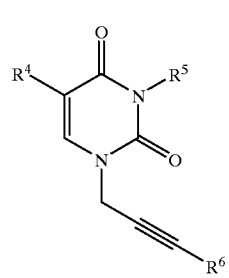

II wherein $R^4$ is hydrogen, chlorine, bromine, iodine, fluorine, —CN, substituted or unsubstituted linear or branched $C_1$–$C_4$ alkyl, —$NO_2$, methoxy, ethoxy, n-propoxy, or iso-propoxy; $R^5$ is hydrogen or propynyl; and $R^6$ is iodine or bromine. Also, methods of preparing these propynyl uracils are provided. The propynyl uracils of the present invention are useful as biocides, including, but not limited to, bactericides, fungicides, and preservatives.

11 Claims, No Drawings

PROPYNYL URACILS

FIELD OF THE INVENTION

This invention relates to propynyl uracils and the use of such compounds as biocides.

BACKGROUND OF THE INVENTION

Ureas and uracils are known to be effective as herbicides and plant growth regulators. See, for example, U.S. Pat. Nos. 5,127,935; 5,354,730; and 5,356,863.

Although there are numerous uracil herbicidal compositions on the market, there is a continuing need for neutral compositions with high biocidal efficacy.

Krivonogov, V. P. et al., *Zh. Prikl. Khim.*, 70(2):315–320 (1997), describe the use of 6-methyl-1,3-di-2-propynyl-2,4 (1H, 3H)-pyrimidinedione in the alkylation of 6-methyluracil and derivatives thereof.

Kundu, Nitya G. et al., *J. Pharm. Sci.*, 71(8):935–8 (1982), disclose the preparation of 1,3-dipropargyl-5-fluorouracil and its use in the preparation of N-alkylated derivatives of 5-fluorouracil.

SUMMARY OF THE INVENTION

Applicants have discovered propynyl uracils having high biocidal activity and methods of preparing such compounds. These compounds are useful as biocides, such as bactericides, fungicides, and preservatives.

Biocidal compositions comprising a microbiocidally effective amount of one or more of the propynyl uracils of the present invention are a further embodiment of the present invention.

Still another embodiment is a method of controlling microorganisms comprising applying a microbiocidally effective amount of one or more propynyl uracils to the microorganisms.

DETAILED DESCRIPTION OF THE INVENTION

The present invention encompasses propynyl uracils having formula I below:

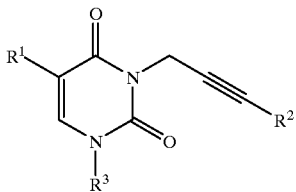

I where $R^1$ is hydrogen, chlorine, bromine, iodine, fluorine, —CN, substituted or unsubstituted linear or branched $C_1$–$C_4$ alkyl, —$NO_2$, methoxy, ethoxy, n-propoxy, or iso-propoxy; $R^2$ is iodine or bromine; and $R^3$ is propynyl, 3-iodopropynyl, 3-bromopropynyl, substituted or unsubstituted 2-furanyl, substituted or unsubstituted 3-furanyl, substituted or unsubstituted 2-pyrrolidinyl, substituted or unsubstituted 3-pyrrolidinyl, D-ribose, or deoxyribose. $R^1$ is preferably hydrogen, methyl, chlorine, bromine, fluorine, or iodine and more preferably chlorine or bromine. $R^3$ is preferably 3-iodopropynyl or 3-bromopropynyl.

Examples of compounds of formula I include, but are not limited to, 1N,3N-bis(3-iodo-2-propynyl)-5-chlorouracil; 1N,3N-bis(3-iodo-2-propynyl)-uracil; 1N,3N-bis(3-iodo-2-propynyl)-5-methyluracil; 1N-(3-iodo-2-propynyl)-3N-(2-furanyl)-5-fluorouracil; 1N,3N-bis(3-iodo-2-propynyl)-5-bromouracil; and 1N,3N-bis(3-bromo-2-propynyl)-5-bromouracil. Examples of more preferred compounds of formula I include, but are not limited to, 1N,3N-bis(3-iodo-2-propynyl)-5-chlorouracil and 1N,3N-bis(3-iodo-2-propynyl)-uracil.

Another embodiment of the invention encompasses propynyl uracils having formula II below:

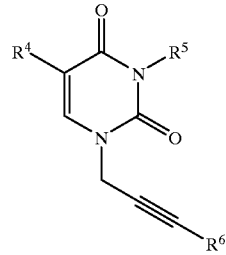

II where $R^4$ is hydrogen, chlorine, bromine, iodine, fluorine, —CN, substituted or unsubstituted linear or branched $C_1$–$C_4$ alkyl, —$NO_2$, methoxy, ethoxy, n-propoxy, or iso-propoxy; $R^5$ is hydrogen or propynyl; and $R^6$ is iodine or bromine. Preferably, $R^6$ is iodine. An example of a compound of formula II is 3N-(3-iodo-2-propynyl)-5-nitrouracil.

The invention further includes a biocidal (or fungicidal) concentrate comprising from about 1 to about 15%, preferably from about 1 to about 5%, by weight of one or more propynyl uracils of the present invention based upon 100% weight of total concentrate. Biocides are materials that prevent the growth of, inhibit the growth of, or kill microorganisms, including, but not limited to, bacteria and fungi.

Generally, the concentrate further comprises from about 1 to about 10%, preferably from about 1 to about 5%, by weight of a solid or liquid formulation adjuvant and up to 15%, preferably from about 0.5 to 10%, by weight of one or more surfactants, based upon 100% weight of total concentrate.

The compositions may also comprise further auxiliaries, such as wetting agents, adhesives, emulsifiers, preservatives, fillers, carriers, viscosity and pH regulators, binders, tackifiers, fertilizers, and other active ingredients. Other conventional adjuvants may be added to the compositions for different applications as known to those of ordinary skill in the art.

The propynyl uracils may be incorporated into different formulations including, but not limited to, granules, pellets, tablets, wettable powders, wettable dusts, microencapsulated materials, impregnated materials, emulsifiable concentrates, flowable concentrates, soluble concentrates, and ready-to-use solutions. The concentrates, granules, pellets, tablets, dusts, and other materials may be diluted with a solvent, such as water, to form a use dilution of the propynyl uracils which may be used as a biocide, such as a bactericide, fungicide, herbicide, or preservative. The use dilution comprises a microbiocidally, bactericidally, or fungicidally effective amount of one or more propynyl uracils of the present invention. Generally, the use dilution comprises from about 0.0005 to about 5% and preferably from about 0.001 to about 0.1% by weight of the propynyl uracils based upon 100% of total use dilution.

Examples of compositions which may contain the propynyl uracils of the present invention include, but are not limited to, personal care products, such as shampoos; wood treatment products; paper products; water treatment equipment; and the like.

Also, the invention includes a method of controlling microorganisms, including bacteria and fungi, comprising applying a microbiocidally, bactericidally, or fungicidally effective amount of one or more of the propynyl uracils of the present invention to the microorganisms.

The propynyl uracils of formula I above may be prepared by reacting a uracil having formula III below:

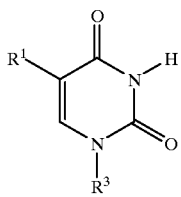

III where $R^1$ and $R^3$ are defined as in formula I with dimethyl formamide, potassium carbonate, and iodopropargyl 4-methylbenzenesulfonate or bromopropargyl 4-methylbenzenesulfonate. Iodopropargyl 4-methylbenzenesulfonate may be prepared as described in European Patent No. EP 539,114-A2.

Alternatively, the propynyl uracils of formula I may be prepared by reacting a uracil of formula III with sodium iodide, dimethyl formamide, potassium carbonate, and propargyl bromide to produce the corresponding 1N-propynyl uracil. The 1N-propynyl uracil is then iodinated or brominated by reacting it with N-iodosuccinimide or N-bromosuccinimide in the presence of silver nitrate to yield the desired propynyl uracil of formula I.

The propynyl uracils of formula II above, where $R^5$ is propynyl, may be prepared by reacting a uracil having the formula

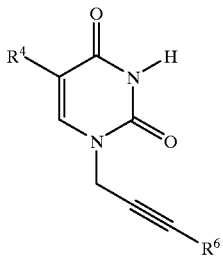

where $R^4$ and $R^6$ are defined as in formula II with sodium iodide, dimethyl formamide, potassium carbonate, and propargyl bromide.

The propynyl uracils of formula II, where $R^5$ is hydrogen, may be prepared by reacting a uracil having the formula

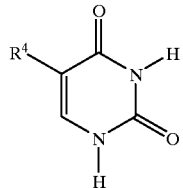

where $R^4$ is defined as in formula II with anhydrous dimethylformamide, potassium t-butoxide, and iodopropargyl-4-methyl-benzene sulfonate or bromopropargyl-4-methyl-benzene sulfonate.

Mixing, adding, and reacting steps in the present invention can be accomplished by conventional means known to those of ordinary skill in the art. The order of addition of reactants or solvent does not affect the process. Reactants and/or solvent can be added sequentially or simultaneously in any suitable reaction vessel. Importantly, the method of the present invention is suitable for commercial scale production techniques and equipment, yet convenient for small scale work.

DESCRIPTION OF THE PREFERRED EMBODIMENTS

The following examples illustrate the invention without limitation. All parts and percentages are given by weight unless otherwise indicated.

EXAMPLE 1

Preparation of 1N,3N-Bis(3-iodo-2-propynyl)-5-chlorouracil 1.5 g of 5-chlorouracil (10.23 mmole) available from Aldrich Chemical Co. of Milwaukee, Wis., 25 mL of dimethyl formamide (DMF), and 2.12 g of potassium carbonate (15.355 mmole) were added to a 100 mL two-necked round bottomed flask. An addition funnel was fitted to one of the necks of the flask and a bubbler was connected to the other neck of the flask to observe carbon dioxide evolution. A solution of 25 mL of DMF and 7.22 g of iodopropargyl 4-methylbenzenesulfonate (21.497 mmole) was added dropwise to the flask through the addition funnel over 2 hours. The iodopropargyl 4-methylbenzenesulfonate was prepared by the method described in European Patent No. EP 539,114-A2. The mixture in the flask was heated to 35° C. and stirred for 36 hours to yield a slurry. The slurry and 200 mL of deionized water were added to a separatory funnel. The mixture was extracted 3 times with 150 mL of chloroform. The chloroform layers were combined and dried with anhydrous magnesium sulfate. The mixture was filtered to remove the chloroform and evaporated under vacuum to yield a brown residue. Chromatography on silica gel with the brown residue was performed using a 1,2-dichloromethane/acetonitrile eluent having a 19:1 volume ratio to yield an off-white solid that was approximately 86% pure. Chromatography was performed a second time with a second silica gel column using a 1,2-dichloromethane/hexanes/acetonitrile eluent having a 1200:600:20 volume ratio to yield 51% of 1N,3N-bis(3-iodo-2-propynyl)-5-chlorouracil as a white solid which was approximately 96% pure.

EXAMPLE 2

Preparation of 1N,3N-Bis(3-iodo-2-propynyl)-uracil

The procedure in Example 1 was repeated, except that a molar eqivalent of uracil available from Aldrich Chemical Co. was used instead of 5-chlorouracil, to produce 1N,3N-bis(3-iodo-2-propynyl)-uracil.

EXAMPLE 3

Preparation of 1N,3N-Bis(3-iodo-2-propynyl)-5-methyluracil

The procedure in Example 1 was repeated, except that a molar eqivalent of 5-methyluracil available from Aldrich Chemical Co. was used instead of 5-chlorouracil, to produce 1N,3N-bis(3-iodo-2-propynyl)-5-methyluracil.

EXAMPLE 4

Preparation of 1N-(3-iodo-2-propynyl)-3N-(2-furanyl)-5-fluorouracil

The procedure in Example 1 was repeated, except that 2.0477 g of 3N-(2-furanyl)-5-fluorouracil (ftorafur) (10.23 mmole) available from Aldrich Chemical Co. was used instead of 5-chlorouracil and 3.6089 g of iodopropargyl 4-methylbenzenesulfonate (10.741 mmole) and 1.060 g (7.67 mmole) of potassium carbonate were used.

EXAMPLE 5

Preparation of 1N-(3-iodo-2-propynyl)-3N-(D-1-ribose)-uracil

The procedure in Example 4 was repeated, except that a molar equivalent of 3N-(D-1-ribose)-uracil (uridine) available from Aldrich Chemical Co. was used instead of 3N-(2-furanyl)-5-fluorouracil.

EXAMPLE 6

Preparation of 3N-(3-iodo-2-propynyl)-5-nitrouracil 1 g of 5-nitrouracil (6.36 mmole) available from Aldrich Chemical Co. and 25 mL of anhydrous dimethylformamide were added to a 100 mL two-necked round bottomed flask. A stir bar was added to the flask and the openings of the flask were fitted with two rubber septa. The mixture was stirred until all solids in the mixture were dissolved. One of the septa was removed and replaced with a silicon oil bubbler attached to a drying tube. The flask was placed in an ice bath to maintain the temperature of the mixture at 5° C. 0.785 g of potassium t-butoxide was added to the mixture by temporarily removing the remaining septum. The mixture was stirred for 1 hour. 2.13 g of iodopropargyl-4-methylbenzene sulfonate was added to the mixture. Then, the mixture was removed from the ice bath, allowed to warm to room temperature, and stirred for 20 hours to form a brown solution. The solution was evaporated under vacuum to yield a brown residue. 30 mL of methanol was added to the residue and the flask was gently swirled in a water bath heated to about 40° C. until only a white solid remained. The solid was vacuum filtered to yield 1.3 g of 3N-(3-iodo-2-propynyl)-5-nitrouracil as crystals. Chromatography was performed with a silica gel column using a hexanes/methylene chloride/ethyl acetate eluent having a 3:2:1 volume ratio to purify the crystals.

EXAMPLE 7

Preparation of 1N,3N-Bis(2-propynyl)-5-bromouracil 5 g of 5-bromouracil (26.18 mmole) available from Aldrich Chemical Co., 0.196 g of sodium iodide (1.31 mmole), and 35 mL of DMF were added to a 200 mL two-necked round bottomed flask. The mixture was stirred for 10 minutes. 5.065 g of potassium carbonate (36.65 mmole) was added to the mixture. Then 8.3687 g of 80% propargyl bromide available from Aldrich Chemical Co. in toluene was added dropwise over 1.5 hours. The mixture was stirred at room temperature for 16 hours to yield a milky solution. The solution was added to a separatory funnel with 200 mL of deionized water and extracted twice with 100 mL portions of 1,2-dichloromethane. The organic layers were combined and dried over magnesium sulfate. The mixture was filtered to remove any solids and evaporated under vacuum to obtain a low volume liquid. The liquid was placed on a Kugelrohr apparatus to remove any DMF in the liquid to yield 1N,3N-bis(2-propynyl)-5-bromouracil as a solid which was approximately 98% pure as determined by HPLC.

EXAMPLE 8

Preparation of 1N,3N-Bis(3-iodo-2-propynyl)-5-bromouracil 0.5 g of 1N,3N-bis(2-propynyl)-5-bromouracil (1.87 mmole) prepared in Example 7, 0.859 g of N-iodosuccinimide (3.820 mmole) available from Aldrich Chemical Co., and 25 mL of acetone were added to a 100 mL recovery flask. The mixture was stirred until all solids were dissolved. 0.0636 g of silver nitrate (0.3745 mmole) was added to the mixture causing a white precipitate to form. After one hour, the mixture was filtered to remove any succinimide by-product. The mixture was evaporated under vacuum to remove any acetone and the remaining residue was mixed with 50 mL of 1,2-dichloromethane until no more solids would dissolve. The mixture was filtered and evaporated under vacuum to yield 1N,3N-bis(3-iodo-2-propynyl)-5-bromouracil as a pale orange solid weighing 0.813 g (approximately 83% yield).

EXAMPLE 9

Preparation of 1N,3N-Bis(3-bromo-2-propynyl-5-bromouracil

The procedure in Example 8 was repeated, except that a molar eqivalent of N-bromosuccinimide available from Aldrich Chemical Co. was used instead of N-iodosuccinimide, to produce 1N,3N-bis(3-bromo-2-propynyl)-5-bromouracil.

EXAMPLE 10

The minimum inhibitory concentrations of 1N,3N-bis(3-iodo-2-propynyl)-5-chlorouracil; 1N,3N-bis(3-iodo-2-propynyl)-uracil; 1N,3N-bis(3-iodo-2-propynyl)-5-methyluracil; 1N-(3-iodo-2-propynyl)-3N-(2-furanyl)-5-fluorouracil; 1N-(3-iodo-2-propynyl)-3N-(D-1-ribose)-uracil; and 3N-(3-iodo-2-propynyl)-5-nitrouracil prepared in Examples 1–6, respectively, were determined against the fungi *Aspergillus niger* by the zone of inhibition assay method common in the art. *A. niger* ATCC #16404 was contacted with each sulfone for 5 days in a Day-Engley neutralizing media. The results are shown in Table 1 below.

TABLE 1

| Propynyl Uracil | 5 Day Minimum Inhibitory Concentration *Aspergillus niger* (mg/L) |
|---|---|
| 1N,3N-Bis(3-iodo-2-propynyl)-5-chlorouracil | 10–30 |
| 1N, 3N-bis(3-iodo-2-propynyl)-uracil | 3–10 |
| 1N, 3N-bis(3-iodo-2-propynyl)-5-methyluracil | 10–30 |
| 1N-(3-iodo-2-propynyl)-3N-(2-furanyl)-5-fluorouracil | 30–100 |
| 1N-(3-iodo-2-propynyl)-3N-(D-1-ribose)-uracil | 100–300 |
| 3N-(3-iodo-2-propynyl)-5-nitrouracil | 30–100 |

EXAMPLE 11

A shampoo having a pH of about 7 and containing 1N,3N-bis(3-iodo-2-propynyl)-5-chlorouracil was prepared having the formulation of Table 2 below.

TABLE 2

1N,3N-Bis(3-iodo-2-propynyl)-5-chlorouracil Shampoo Formulation

| Ingredient | Parts (by weight) |
|---|---|
| Sodium Lauryl Ether Sulfate | 35.0 |
| Triethanolamine Lauryl Sulfate | 25.0 |
| Cocamide DEA | 3.0 |
| PolyPro 5000 ™* (hydrolyzed collagen) | 1.0 |
| Sterile Deionized Water | 36.0 |
| 10.0% Citric Acid | 0.3 |
| 1N,3N-Bis(3-iodo-2-propynyl)-5-chlorouracil | 0.05 |
| Total | 100.35 |

*PolyPro 5000 ™ is available from Hormel & Co. of Austin, MN.

EXAMPLE 12

The fungicidal efficacy of the shampoo formulation containing 1N,3N-bis(3-iodo-2-propynyl)-5-chlorouracil prepared in Example 11 was determined as follows. A mixture of a 48 hour culture of *Candida albicans* and 7 to 14 day culture of *Aspergillus niger* was prepared. The shampoo was inoculated with the mixture of fungi and incubated at room temperature for 28 days. The number of colony forming units present in the shampoo after 0, 14, and 28 days was determined by neutralizing a small amount of the inoculated shampoo with Day-Engley neutralizing broth and adding serially diluted samples of the broth to dextrose agar plates. The plates were incubated for 3 to 5 days.

This procedure was repeated with Glydrant Plus® Liquid available from Lonza Inc. of Annandale, N.J., as well as with the shampoo formulation prepared in Example 11 without 1N, 3N-bis(3-iodo-2-propynyl)-5-chlorouracil, i.e., a preservative free shampoo.

The results are shown in Table 4 below.

TABLE 4

| | Mixture of *Candida albicans* and *Aspergillus niger* (cfu/mL) | | |
|---|---|---|---|
| Day | 1N,3N-Bis(3-iodo-2-propynyl)-5-chlorouracil Shampoo | Glydant Plus ® Liquid | Control Preservative Free Shampoo |
| 0 | 1 × 10$^5$ | 2 × 10$^5$ | 2 × 10$^5$ |
| 14 | <10 | <10 | 1 × 10$^5$ |
| 28 | <10 | <10 | 1 × 10$^5$ |

EXAMPLE 13

1N,3N-bis(3-iodo-2-propynyl)-5-chlorouracil was tested against the wood-rotting fungi *Trametes versicolor* (a white rot; ATCC 42462), *Gloephyllium trabeum* (a brown rot, ATCC 11539), *Postia placenta* (a brown rot, ATCC 11538), and *Chaetomium globosum* (a soft rot, ATCC 6205) as follows. The Agar Plate Dilution method described in Schultz, T. P. et al., Comparison of the fungicidal activities of (E)-4-hydroxylated stilbenes and related bibenzyls, *Phytochemistry* 30:2939–45 (1991), and Archer, K. D. et al., Screening of Wood Preservatives: Comparison of the Soil Block, Agar-Block, and Agar-Plate Test, *For. Prod J.* 45(1):86–9 (1995), was performed to determine the minimum concentration of uracil necessary to achieve a 50% zone of inhibition over 9 days of contact time.

This test was repeated substituting didecyldimethyl ammonium chloride, available as Bardac® 2280 from Lonza Inc. of Fair Lawn, N.J., for 1N,3N-bis(3-iodo-2-propynyl)-5-chlorouracil The results are shown in Table 5 below.

TABLE 5

| Organism | IC$_{50}$ (ppm) for didecydimethyl ammonium chloride | IC$_{50}$ (ppm) for 1N,3N-bis(3-iodo-2-propynyl)-5-chlorouracil |
|---|---|---|
| *C. globosum* | 62.9 | 3.22 |
| *P. placenta* | 5.6 | <5.0 |
| *G. trabeum* | 6.45 | 3.22 |
| *T. versicolor* | 53.9 | 6.12 |

A total kill was observed for *T. versicolor, G. trabeum,* and *P. placenta* at no more than about 50 ppm of 1N,3N-bis(3-iodo-2-propynyl)-5-chlorouracil.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A compound having the formula

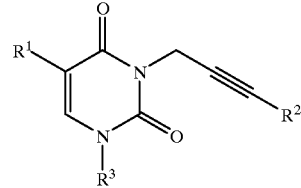

wherein R$^1$ is hydrogen, chlorine, bromine, iodine, fluorine, —CN, linear or branched C$_1$–C$_4$ alkyl, —NO$_2$, methoxy, ethoxy, n-propoxy, or iso-propoxy; R$^2$ is iodine or bromine; and R$^3$ is propynyl, 3-iodopropynyl, 3-bromopropynyl, 2-furanyl, 3-furanyl, 2-pyrrolidinyl, or 3-pyrrolidinyl.

2. The compound of claim 1, wherein R$^1$ is selected from the group consisting of hydrogen, methyl, chlorine, bromine, fluorine, and iodine.

3. The compound of claim 1, wherein R$^3$ is selected from the group consisting of 3-iodopropynyl.

4. The compound of claim 1, wherein R$^3$ is selected from the group consisting of 3-bromopropynyl.

5. The compound of claim 2, wherein R$^1$ is chlorine or bromine, R$^2$ is iodine, and R$^3$ is 3-iodopropynyl.

6. The compound of claim 5, wherein R$^1$ is chlorine.

7. The compound of claim 5, wherein R$^1$ is bromine.

8. A method of controlling fungi comprising applying a fungicidal effective amount of one or more compounds of claim 1 to the fungi.

9. A fungicidal composition comprising a fungicidally effective amount of one or more compounds of claim 1 and a solvent.

10. The fungicidal composition of claim 9, wherein the inert carrier comprises a solvent.

11. The fungicidal composition of claim 10, wherein the solvent is water.

* * * * *

UNITED STATES PATENT AND TRADEMARK OFFICE
CERTIFICATE OF CORRECTION

PATENT NO.    : 6,344,460 B1
DATED         : February 6, 2002
INVENTOR(S)   : Nirchio It is certified that error appears in the above-identified patent and that said Letters Patent is hereby corrected as shown below:

Title page,
Please add item -- [60] Related U.S. Application Data -- and insert -- Provisional application No. 60/125,289  03/19/99 --.

Column 1,
Line 2, after the title, insert -- RELATED APPLICATION
This application claims benefit of U.S. Provisional Patent Application No. 60/125,289, filed March 19, 1999 --.

Signed and Sealed this

Twenty-second Day of October, 2002

Attest:

Attesting Officer

JAMES E. ROGAN
*Director of the United States Patent and Trademark Office*